United States Patent [19]

Aizu et al.

[11] Patent Number: 4,952,050
[45] Date of Patent: Aug. 28, 1990

[54] OPHTHALMOLOGICAL DIAGNOSIS METHOD AND APPARATUS

[75] Inventors: Yoshihisa Aizu, Machida; Kouji Ogino; Toshiaki Sugita, both of Hino, all of Japan

[73] Assignee: Kowa Company Ltd., Japan

[21] Appl. No.: 337,393

[22] Filed: Apr. 13, 1989

[30] Foreign Application Priority Data

Apr. 15, 1988 [JP] Japan .................................. 63-91672

[51] Int. Cl.$^5$ ............................ A61B 3/10; A61B 3/14
[52] U.S. Cl. .................................... 351/221; 351/211; 351/206; 128/691
[58] Field of Search ............... 351/205, 206, 213, 214, 351/211, 221, 246; 128/691; 606/4, 5, 6

[56] References Cited

U.S. PATENT DOCUMENTS 4,402,601  9/1983  Riva ................................. 351/221 X
4,423,931  1/1984  Shapiro ........................... 351/211 X Primary Examiner—Rodney B. Bovernick
Attorney, Agent, or Firm—Bruce L. Adams; Van C. Wilks

[57] ABSTRACT

Disclosed is an ophthalomological diagnosis method and apparatus in which a blood vessel in the eye fundus is illuminated with a laser beam of a predetermined beam spot whose diameter is substantially equal to or smaller than that of the blood vessel in order to produce diffraction-plane speckles which are formed at a Fourier-transform plane by light scattered from the eye fundus. Boiling motion of the diffraction-plane speckle pattern thus produced is then detected through a multiple detection aperture pattern which is disposed at the Fourier-transform plane and comprised of a plurality of small apertures to obtain a speckle signal which is evaluated to measure velocity of the blood flowing through the blood vessel concerned. This arrangement makes it possible to detect the speckle signal without any effect of averaging the signal with an increase in intensity detected, thus enabling advantageous and successful measurement of the blood flow state in the eye fundus.

13 Claims, 9 Drawing Sheets

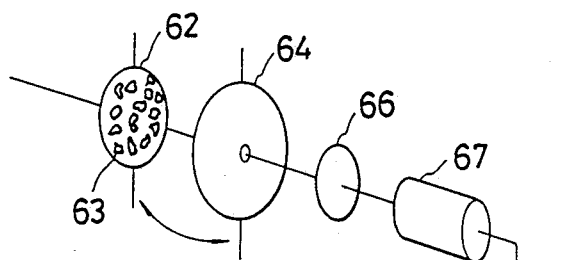
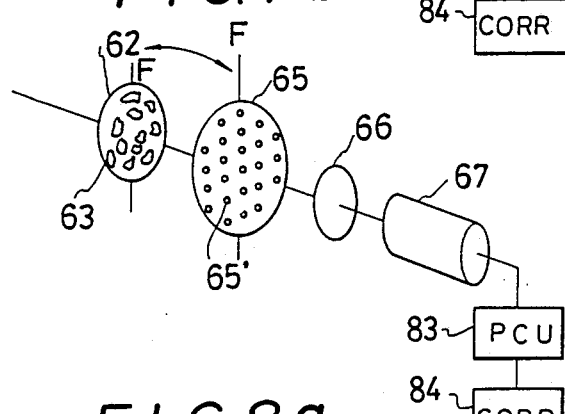
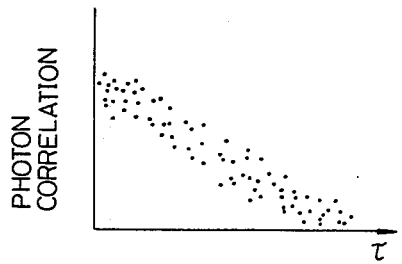
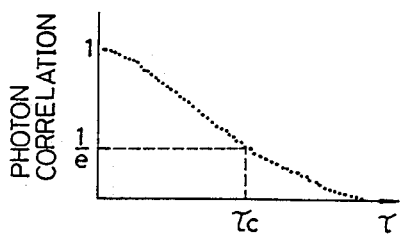
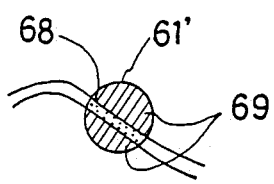
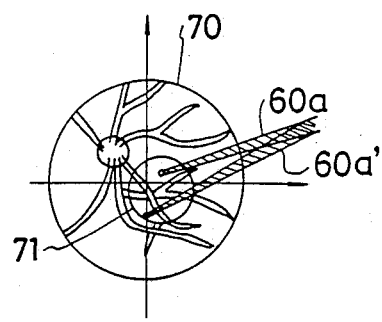
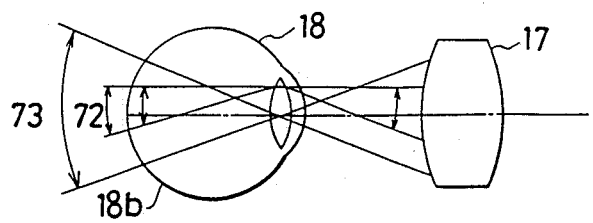

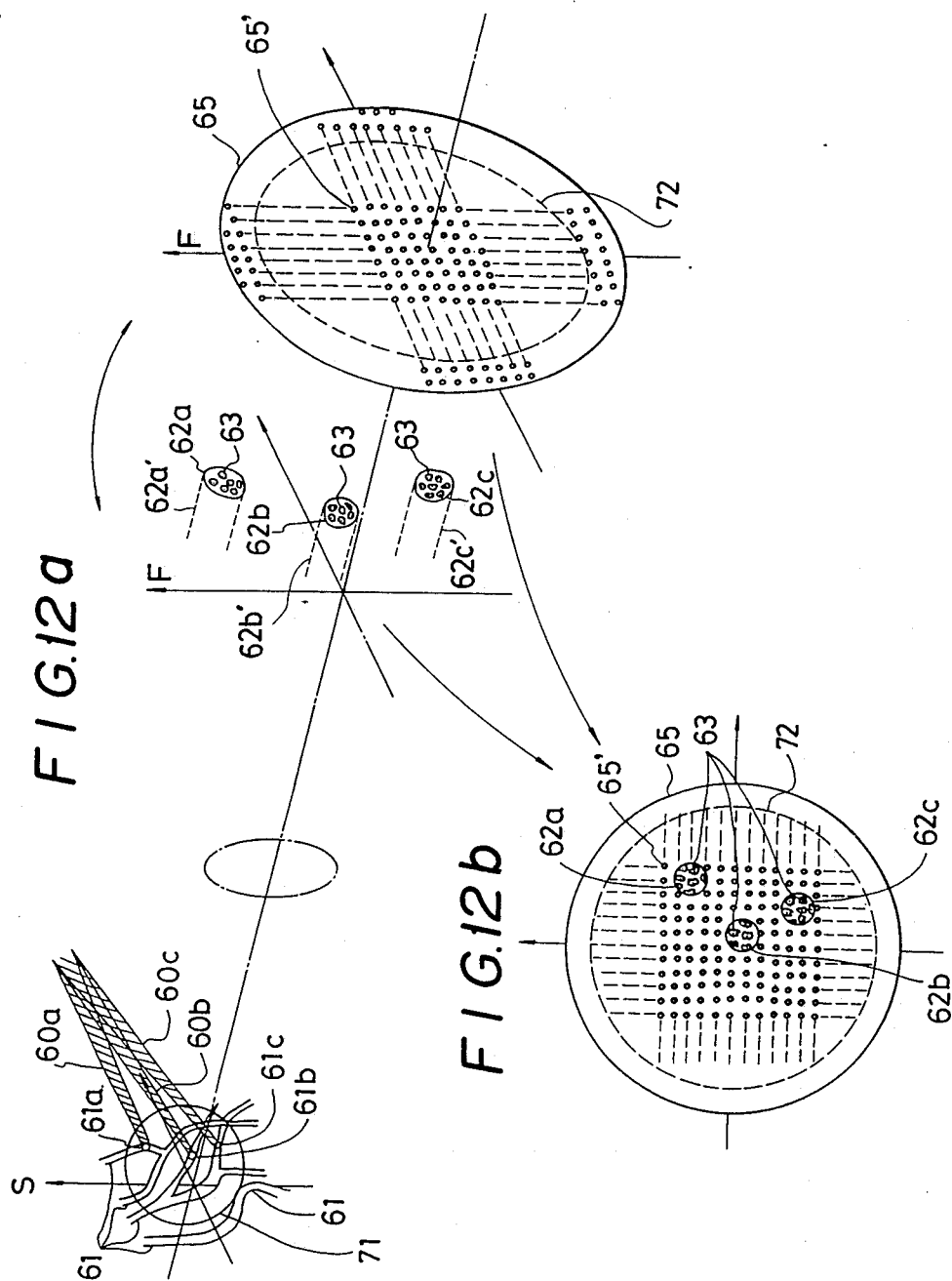

FIG.17a   FIG.17b   FIG.17c
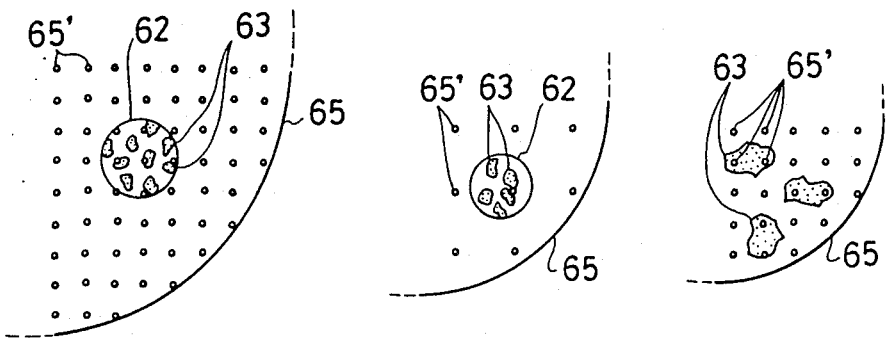
FIG.17d   FIG.17e
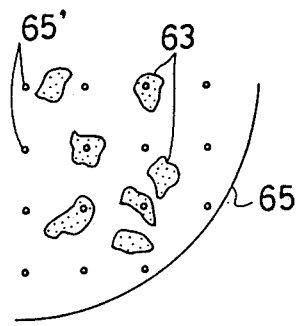 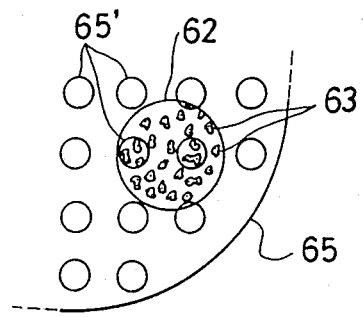
FIG.18a   FIG.18b
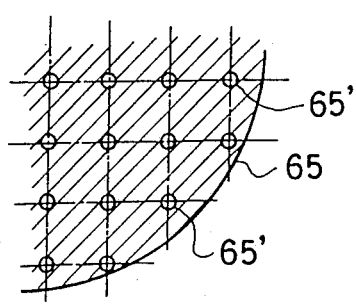 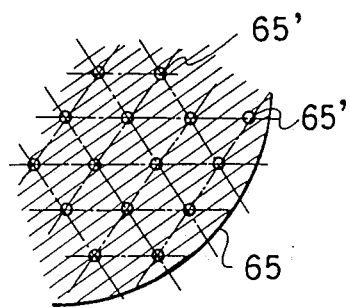

OPHTHALMOLOGICAL DIAGNOSIS METHOD AND APPARATUS

BACKGROUND OF THE INVENTION

1. Field of the Invention

This invention relates to an ophthalmological diagnosis method and apparatus, and more particularly to an ophthalmological diagnosis method and apparatus in which the eye fundus is illuminated by a beam of laser light having a predetermined diameter, and scattered laser light reflected from tissue in the eye fundus is evaluated to measure the blood flow state for ophthalmological diagnosis.

2. Description of the Prior Art

Conventional methods that employ laser light to measure the state of the blood flow in the eye fundus include those disclosed in Japanese Patent Laid-open Publications Nos. 55(1980)-75668, 55(1980)-75669, 55(1980)-75670, 56(1981)-125033 and 58(1983)-118730. All of these are methods for determining blood flow velocity based on the laser Doppler effect, so in each case it is therefore necessary to detect the frequency shift of the laser light caused by the Doppler effect. This can be done using either of two arrangements. One comprises splitting the incident laser beam into two beams forming equal angles with respect to the optical axis of the incident laser beam and directing the split beams into the eye to be examined so that they intersect precisely at the position of the eye fundus blood vessel concerned. The other arrangement is to detect laser light scattered by the eye fundus blood cells from two different directions. In both cases the optical system is complex and needs to be high-precision. In addition, the fact that the angle of beam incidence or light detection has to be known in advance makes these methods extremely difficult to apply clinically because of dependency of the eyes to be examined upon patients and impairs the repeatability and reliability of the results thereby obtained. This shows that the laser Doppler method is very useful for application in the industrial field having stable and steady objects because of its precise and sensitive features, but is apt to be influenced by various factors and disadvantageously reduces the repeatability of the results obtained, particularly in the medical field in which biological organisms living in unstable atmospheres and conditions are to be examined.

Further, in actual measurements the results are not obtained as a single Doppler shift frequency but consists of wide-ranging frequency components extending from the low to high frequency region, making it difficult to obtain a reliable absolute velocity value.

Other problems arise from the fact that the laser beam can be directed onto the eye fundus only along path that are perpendicular or nearly perpendicular to the eye fundus. At such angles, the Doppler shift is very small and the beat signals are hard to detect. This is because the laser Doppler method requires the detection of a single beat component. Thus in applications relating to biological tissues, which produce a wide range of irregular interferences, it is preferable to make use of the laser speckle method, the very essence of which is the interference effect of irregularly scattered light.

It is known that when a laser beam strikes an object which causes diffusion or scattering of the beam, the light scattered from the object generally gives rise to a speckle pattern caused by interference between reflected rays of the coherent light. In this case, any movement of the object causing the scattering will cause motion of the speckle pattern which can be detected as a time-course change in light intensity at an observation point. Thus, if the changes in intensity are converted into a signal, it becomes possible to measure the movement of the light-scattering object from the signals. The present invention applies this principle to the measurement of the state of blood flow in living tissue such as, for example, the tissue constituting the eye fundus.

Japanese Patent Laid-open Publications Nos. 60(1985)199430, 60(1985)-203235 and 60(1985)-203236, for example, disclose an application of such speckle phenomena to the measurement of the blood flow. These methods, however, intend to apply in the measurement on the skin surface and thus are inapplicable to the measurement of the blood flow in the eye funds in view of the facts of radiation of a laser beam in a certain intensity and the necessity of a corresponding detection optical system.

For this reason, the inventors have already filed an application for the invention entitled ophthalmological diagnosis method and apparatus (corresponding to U.S. Pat. No. 4,743,107) in which a laser speckle pattern is used to measure the blood flow in the eye fundus. In this method, however, a region of the eye is illuminated with a laser beam having a predetermined diameter greater than that of one blood vessel in the eye, and light scattered from a plurality of blood vessels within the illuminated region of the eye is detected at the Fraunhofer diffraction plane at which the scattered light is superimposed to produce a speckle pattern whose motion is detected, thus improving the stability and repeatability of the measurement obtained. Thus, this method is advantageous because its arrangement enables an overall, average evaluation of the state of blood flow in a plurality of blood vessels included within the irradiated region of the eye, but is impractical when the velocity of blood flow in a single specific blood vessel within the irradiated region is to be measured.

To overcome this drawback, the same inventors proposed an improved ophthalmological diagnosis apparatus using a laser speckle method which makes use of a new detection system so as to be able to evaluate the blood flow velocity of a specified blood vessel. This apparatus is disclosed, for example, in Japanese Patent Laid-open Publications Nos. 63(1988)-242220 and 63(1988)-242221. This, however, disadvantageously requires a detection aperture (for example, pin hole or slit) which must be set on a blood vessel image to be measured at a magnified image plane in order to select one of the specified blood vessels. Further, the detection plane is at an image plane and conjugate with the eye fundus, thus causing the displacement of the image position as the portion of the eye fundus to be measured displaces. This necessitates means for observing the eye fundus image by naked eye for alignment. For this purpose, an observing eyepiece is provided with an indicating mark, which is aligned within its view field to the position of a blood vessel concerned to cause the detection aperture to displace by a mechanical interlocking mechanism in response to the adjustment of the indicating mark for alignment into the position of the corresponding blood vessel image at the magnified image plane. Thus it has been found that the interlocking mechanism is complicated with the total apparatus cost increased, and the mechanical adjustment at the manufacturing between the indicating mark and the detection aperture is also sophisticated. The mechanical interlocking mechanism further includes a mechanical play, causing position setting errors and a poor operational responsibility. Furthermore, there is the necessity of a two-stepped operation to specify blood vessels concerned. One is to carry out positional alignment with the aid of an eye fixation target to illuminate a region including the blood vessels with the laser beam. And the other is to specify one of the blood vessels with the aid of the indicating mark on the eyepiece. This disadvantageously causes a detected position to deviate during the period of the above-mentioned alignment because of the movement of the patient's eye, thus needing renewed alignment or adjustment.

On the other hand, the laser beam is projected on a region of the eye fundus extending over an area greater than the diameter of the blood vessel. This produces light which is scattered from the surrounding tissue outside the blood vessels within the illuminated region of the eye fundus and is greater in intensity than light scattered from the blood flow cells flowing in the blood vessel, thereby making it difficult to clearly discriminate the blood vessel and the surrounding tissue at the magnified image plane. To overcome this drawback, a filtering at the spatial frequency plane is proposed, but this also disadvantageously causes the optical system to be complicated and the quantity of detected light to be reduced greatly.

Furthermore, a speckle pattern of sufficient intensity can not be detected because the eye fundus has too low reflectivity and because observation and photography optical systems used in an eye fundus camera have a large F-number and this makes detected light intensity too small. However, a too strong laser beam cannot be projected onto the eye fundus from the point of view of safety. Thus, a photon correlation method useful to detect light of a very weak intensity has been proposed as shown in Japanese Patent Laid-open Specifications Nos. 62(1987)-275431 (corresponding to U.S.P. 4,743,107) and 63(1988)-242220.

This method is, however, impractical in view of the fact that a detection plate having an aperture sufficiently smaller than the average size of the individual speckles must be set at the detection plane so as to be able to detect the changing light intensity distribution of the speckle pattern sharply. This inevitably causes the reduction of the light detected and necessitates a measurement time (so long as ten to several tens seconds) to obtain sufficiently converged and stabilized photon correlation data. For this reason, the quantity of light projected on the patient's eye increases. The patient should further be under heavy burdens that he must be stationary during measurement. This actually causes the eye movement, thus making the measurement incorrect.

On the other hand, a method has been proposed in which the diameter of the detection aperture is made greater to increase the light detected. This, however, causes an increase in DC component whose rate is much greater than the increase rate of the effective signal components, thus resulting in undesired reduction of an S/N ratio and poor converging stability of photon correlation data.

SUMMARY OF THE INVENTION

It is, therefore, an object of the present invention to provide an ophthalmological diagnosis method and apparatus enabling accurate and effective measurement of the state of blood flow in blood vessels in the eye tissue.

It is another object of the present invention to provide an ophthalmological diagnosis method and apparatus enabling easy and accurate measurement of the velocity of blood flowing through a single specific vessel in the eye fundus, using a laser speckle method.

According to the invention, the eye fundus is illuminated with a laser beam of a predetermined diameter, and light scattered and reflected from the eye fundus is evaluated to measure the blood state in the eye fundus tissue.

More particularly, a blood vessel to be measured is illuminated with the laser beam of a predetermined beam spot whose diameter is substantially equal to or smaller than that of the blood vessel. Light scattered and reflected by blood cells flowing through the blood vessel illuminated by the laser beam is converged to form diffraction-plane speckles at a Fourier-transform plane relative to the eye fundus which is taken as an object plane. Boiling motion of the diffraction-plane speckles is then detected through a detection aperture disposed at the Fourier-transform plane and formed thereon with a multiple detection aperture pattern comprised of a plurality of small apertures. A speckle signal produced by a photodetector depending upon a fluctuation in a total amount of light passing through each of the small apertures on the multiple detection aperture pattern is evaluated to measure velocity of the blood flowing through the blood vessel concerned.

With such an arrangement, the laser beam can be adjusted in its spot diameter at the beginning of measurement so as to be substantially equal to or smaller than the diameter of the blood vessel concerned, and then projected onto the blood vessel to be measured. This enables the laser beam to be aligned easily to the blood vessel by a single manipulation of the laser beam spot. The laser beam is almost all scattered and reflected from the blood flow and very few scattered from the surrounding tissues, so that the speckle light converged at the speckle detection plane can all be used for signal evaluation. This is particularly preferable for photon correlation detection because it processes very weak light. If the laser speckles are simply detected by a single aperture of a great diameter, there may be the fear of averaging the intensity fluctuation of the distributed speckles with the result of a great reduction in S/N ratio. The invention, on the other hand, makes use of a multiple detection aperture pattern comprised of a plurality of small apertures. This enables a signal detection without any effect of averaging the signal and leads to an increase in intensity detected, so that the speckle light whose primary components are made of the light scattered from the blood vessel can be utilized advantageously and successfully when the photon correlation method is employed instead of usual photoelectrical detection methods.

Disclosed in the Japanese magazine "Kougaku(Optics)" Vol. 11, No, 3(1982, June), pages 291 to 297, is use of a plurality of detecting apertures for detecting speckle motion, in which speckles concerned cause translational motion, that is, the speckle pattern at the plane of detection shifts translationally with its pattern unchanged even if the object moves. In such movement, a cross-correlation component may be disadvantageously detected by any of the two apertures disposed in neighborhood in a direction along which the speckles move, thus making the signal component different than in the detection of the speckle light using a single aperture. To reduce this disadvantageous influence, it is necessary to make a distance between the two apertures sufficiently great. As a result, many small apertures cannot be disposed effectively for light detection.

On the other hand, the present inventors have found that the motion of laser speckle pattern formed by the light scattered and reflected from the eye fundus is boiling motion in which the speckles at the detection plane effect no translational motion even if the object moves, but fluctuate in flickering manner with their positions unchanged but its shape changed. We are thus proposing to make use of a multiple detection aperture pattern comprised of a plurality of small apertures in order to detect the boiling motion. Since the boiling motion is free of an influence due to the cross-correlation caused by the adjacent apertures and since many small apertures can be arranged on the detection aperture, various advantages can be obtained. It is needless to say that errors due to the positional deviation caused by eye movement during measurement can be reduced because of great increase in intensity of detected light and because of a reduced measuring time, thus greatly reducing a burden on the patient and providing preferable measurement results from the point of view of safety.

The present inventors have also proposed a similar method for detecting motion of the speckles using an aperture pattern having small apertures as disclosed in Japanese Patent Laid-open Publication No. 63(1988)-82365, in which the apertures are arranged at random to form a random pattern. The signal components greatly depend upon how the pattern is manufactured at random or how many apertures it has, so that it would be impractical in view of repeatability and stability to derive the same signal components when many random patterns are used. The irregular distribution of intensity caused by the random pattern and appearing at the plane of detecting the speckle light is a factor that cannot be neglected. In contrast to this, the invention makes use of a multiple detection aperture pattern of small apertures which are disposed in a regularly arranged array to overcome the above-mentioned drawbacks.

The speckle patterns are grouped into a diffraction-plane speckle pattern formed at a Fourier-transform plane relative to the eye fundus taken as an object plane and an image-plane speckle pattern formed at an image plane that is conjugate with the eye fundus. Principally, the detection plane can be set either on the Fourier or image plane for the invention in which boiling motion of the speckle light formed by only light scattered from the blood vessel concerned is detected at the detection plane by means of a multiple detection aperture pattern. In the image plane speckles, however, the spot size of the laser beam is very small, more particularly so small as 150 to 200 micrometers in diameter, and is substantially equal to or smaller than the diameter of the blood vessel. This means that a spot image formed by the speckle light at the image plane is the same size if it is imaged in equal size, thus making the averaged size of each of the individual speckles much smaller. In addition, it is necessary that each diameter of the apertures on the multiple detection aperture pattern is less than the average speckle size because a reduction in contrast due to the signal averaging by integral must be avoided. As a result, it is necessary to use a multiple detection aperture pattern comprised of a plurality of very small apertures (several micrometers in diameter). This is however impractical in view of the fact that such an aperture pattern is difficult to manufacture, expensive and sophisticated in handling and management against dusts or the like. To compensate for this, a method may be proposed in which a microscopic objective is used for magnification to provide detection at a conjugate and magnified image plane. This method is, however, not suitable because the incorporation of a magnification imaging system using the microscopic objective into the speckle detecting optical system inevitably makes the optical path longer by an amount of 100 to 150 mm and the whole apparatus complicated by a factor that the optical path must be set considering an optical path due to the beam reflection by mirrors. This method also has the drawback that a slight deviation of the objective causes a great displacement of the magnified image. The invention solves this problem by setting the detection plane on the Fourier-transform plane.

BRIEF DESCRIPTION OF THE DRAWINGS

The objects and features of the present invention will become more apparent from a consideration of the following detailed description taken in conjunction with the accompanying drawings in which:

FIGS. 7a and 7b are perspective views of signal detection arrangements;

FIGS. 8a and 8b are photon correlation functions of speckle signals obtained from the configurations of FIGS. 7a and 7b, respectively;

FIG. 9 is an explanatory diagram illustrating the illumination of a blood vessel by a laser beam;

FIG. 10 is a drawing illustrating the observation and photography field of view;

FIG. 11 is a drawing illustrating the conditions that limit the observation and photography field of view;

FIGS. 12a and 12b are drawings illustrating speckles at a Fourier-transform plane;

FIGS. 17a to 17e are drawings illustrating the relationship between speckles and detection apertures;

FIGS. 18a and 18b show detection aperture arrangements;

DETAILED DESCRIPTION OF THE PREFERRED EMBODIMENTS

The invention will now described in detail with reference to the drawings.

While the embodiments described in the following relates to the application of the invention to ophthalmological diagnosis involving the use of an eye fundus camera to measure blood flow in the tissue of the eye fundus, the invention is not limited to such application and can be applied in a wide range of other forms of ophthalmological examination as well.

Figure 1:
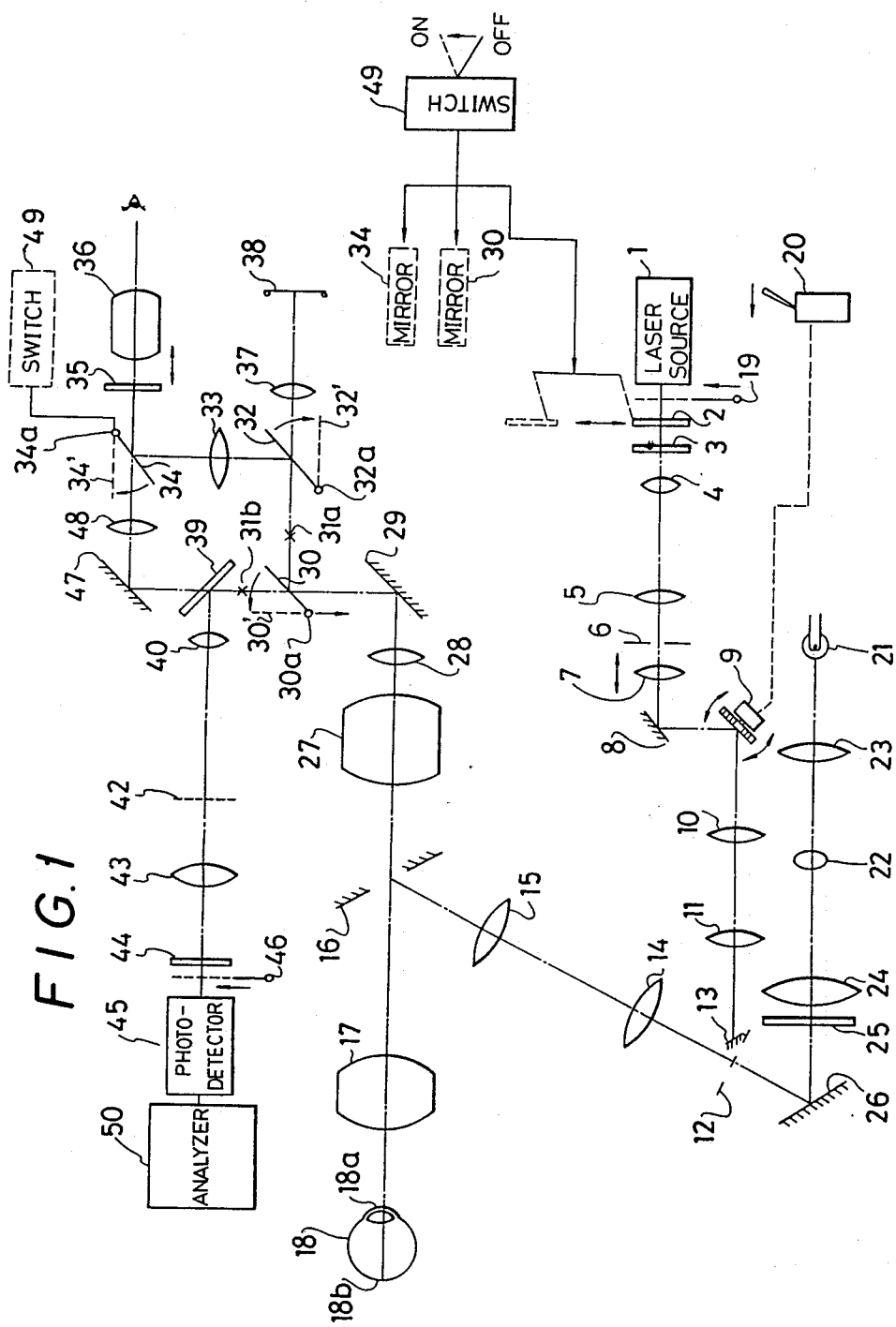
FIG. 1 is a diagram showing the overall structure of the apparatus according to the present invention.
Figure 2:
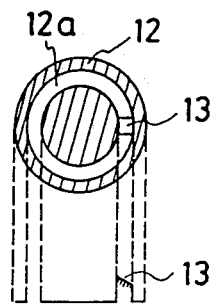
FIG. 2 is a diagram illustrating the structure of a ring slit used in the apparatus of FIG. 1.

In FIG. 1, a laser beam such as from a red-light He-Ne (wavelength: 632.8 nm) type laser beam source 1 is passed through two light quantity adjustment filters 2 and 3 and a condenser lens 4, and is then formed into a parallel beam by a collimating lens 5. Following this, the beam is set to a suitable diameter by an aperture 6 and passes through a laser focusing lens 7 which is for adjusting the size of the area the beam illuminates on a fundus 18b of an eye 18 under examination. The beam is then directed via a mirror 8 and a swingable mirror 9 to pass through relay lenses 10 and 11. As shown in FIG. 2, the laser beam issuing from the relay lens 11 is reflected by a mirror 13 provided in one portion of an annular aperture 12a formed in a ring slit 12 disposed in the eye fundus illuminating projector, so that the reflected laser beam travels along the same light path leading to the eye fundus under examination as that followed by a beam of light directed onto the eye fundus to provide illumination for photography and observation. As a result, the laser beam passes through relay lenses 14 and 15, and via a ring mirror 16 and objective 17 passes through a cornea 18a of an eye 18 under examination to impinge on the fundus 18b of the eye, illuminating the blood vessels to be measured.

Disposed near the beam-emitting end of the laser beam source 1 is a shutter 19 which can be opened or closed as required. The swingable mirror 9 is for changing the position of the beam on the fundus, and is operated by a manipulator 20, for example. The swingable mirror 9 can be utilized by means of a method used in an ordinary coagulator or the like whereby the angle of the mirror is changed independently in the x and y directions, relative to the optical axis.

As is known, by locating the swingable mirror 9 at a position that is a conjugate of the cornea or pupil, the position of the beam on the fundus can be changed without largely altering the position at which the beam impinges on the cornea of the eye under examination 18.

This measurement region is also illuminated by the illuminating projector of the fundus camera, facilitating observation. The system for providing the illumination for observation is constituted of an observation light source 21, a condenser lens 23, a condenser lens 24, a filter 25 and a mirror 26 disposed on the same light path as a photographic light source 22. Having the path of the laser beam coincide with that of the beam of photographic and observation light is convenient, because by means of the swingable mirror 9 the laser beam can be made to impinge on the desired region of the eye fundus 18b by using the mechanisms for swinging and tilting the eye fundus camera vertically and horizontally and the eye fixation means.

Figure 3:
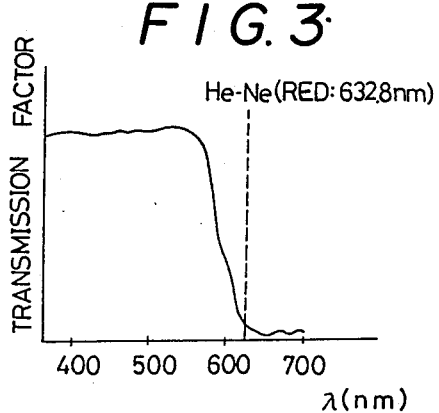
FIG. 3 is a characteristic curve showing the characteristics of a filter used in the apparatus of FIG. 1.

The filter 25 disposed between the condenser lens 24 and the mirror 26 is a wavelength separation filter having the type of characteristics shown in FIG. 3 to filter out red components from the observation and photographic light. A filter is selected that has spectral characteristics appropriate to the wavelength of the laser beam source that is employed.

Speckle light produced when the laser beam is scattered by blood cells moving in the target blood vessels in the eye fundus, together with reflected observation and photographic light, passes through the objective 17, the ring mirror 16, a focusing lens 27, a relay lens 28, a mirror 29 and a swingable mirror 30, whereby the light is formed into an image at a point on an image plane 31a. This image can be observed by a zoom-type eyepiece 36, which can be adjusted to allow operators with varying visual capabilities to focus on the reticle 35.

To photograph the light, the swingable mirror 32 is pivoted about a point 32a in the direction indicated by the arrow to raise it to a position 32', whereby the observation and photographic light including speckle light from the fundus that is reflected by the swingable mirror 30 is formed into an image on -photographic film 38 by the imaging lens 37. Thus, the system can be used for observation and photography of the fundus like an ordinary fundus camera. The ability to observe and photograph the fundus when it is being illuminated by the laser beam is highly convenient, as it enables the measurement point to be directly confirmed and filmed.

For measuring blood flow, the swingable mirror 30 interlocked with a measurement switch 49, described below, is pivoted up about a point 30a to position 30', and at the same time another swingable mirror 34 that is also interlocked with the measurement switch 49 is pivoted up about a point 34a to position 34'. As a result, the speckle light from the fundus reflected by the mirror 29 and observation and photographic light is formed into an image at a spatial plane point 31b that is optically equivalent to the image point 31a. Downstream of the point 31b is a wavelength separation mirror 39 fixed at an angle of about 45 degrees relative to the optical axis. Like the wavelength separation filter 25, the wavelength separation mirror 39 has the same kind of spectral characteristics shown in FIG. 3 and therefore reflects most of the speckle light (red) produced by the He-Ne laser beam.

The reflected speckle light passes via a Fourier-transform lens 40 and forms on a multiple detection aperture pattern 42 a diffraction-plane speckle pattern which is formed by only the light scattered from just the region of the fundus blood vessels illuminated by the laser beam. The multiple detection aperture pattern 42 is constituted of a plurality of small apertures and disposed at a plane of Fourier transform with respect to the eye fundus. The speckle light from the multiple detection aperture pattern 42 is converged by a condenser lens 43, passes through an interference filter 44 which blocks light having a wavelength other than the 632.8 nm red light produced by the He-Ne laser, and impinges on a photodetector 45 constituted of a photomultiplier for counting photons produced. A shutter 46 is disposed in front of the photodetector 45. The photoelectrical pulse signal produced by the photodetector 45 when the shutter 46 is open is input to an analyzer section 50.

The observation and photography light, other than red component light, and a small amount of speckle light that is transmitted by the wavelength separation mirror 39 passes via relay lenses 47 and 48 to form an image of the fundus at the reticle 35. This image can be observed by means of the zoom-type eyepiece 36 described above. The ability to thus observe the fundus during blood flow measurement is highly effective for preventing errors such as performing measurements without noticing that the part concerned has shifted position.

Figure 4:
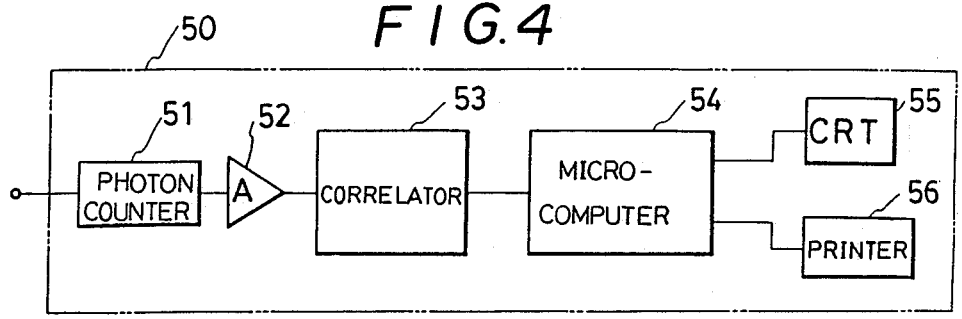
FIG. 4 is a block diagram of a signal processor.

As shown in FIG. 4, the analyzer section 50 is constituted of a photon counting unit 51, an amplifier 52, a correlator 53, a microcomputer 54, a CRT display 55 and a printer 56.

Figure 5:
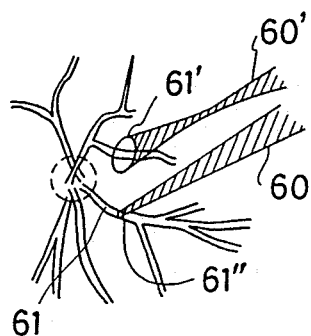
FIG. 5 is an explanatory diagram illustrating the illumination of blood vessels in an eye fundus.

The basic principle employed to evaluate blood flow velocity with the above arrangement will now be described. With reference to FIG. 5, a portion 61″ of a fundus retinal blood vessel 61 to be measured is illuminated by a laser beam 60. By means of the light receiving system illustrated in FIG. 1, the light scattered from the illuminated portion 61″ to be measured forms a diffraction-plane speckle pattern on the multiple detection aperture pattern 42 (FIG. 1) which is comprised of a plurality of small apertures and disposed at the Fourier-transform plane relative to the eye fundus.

Figure 6:
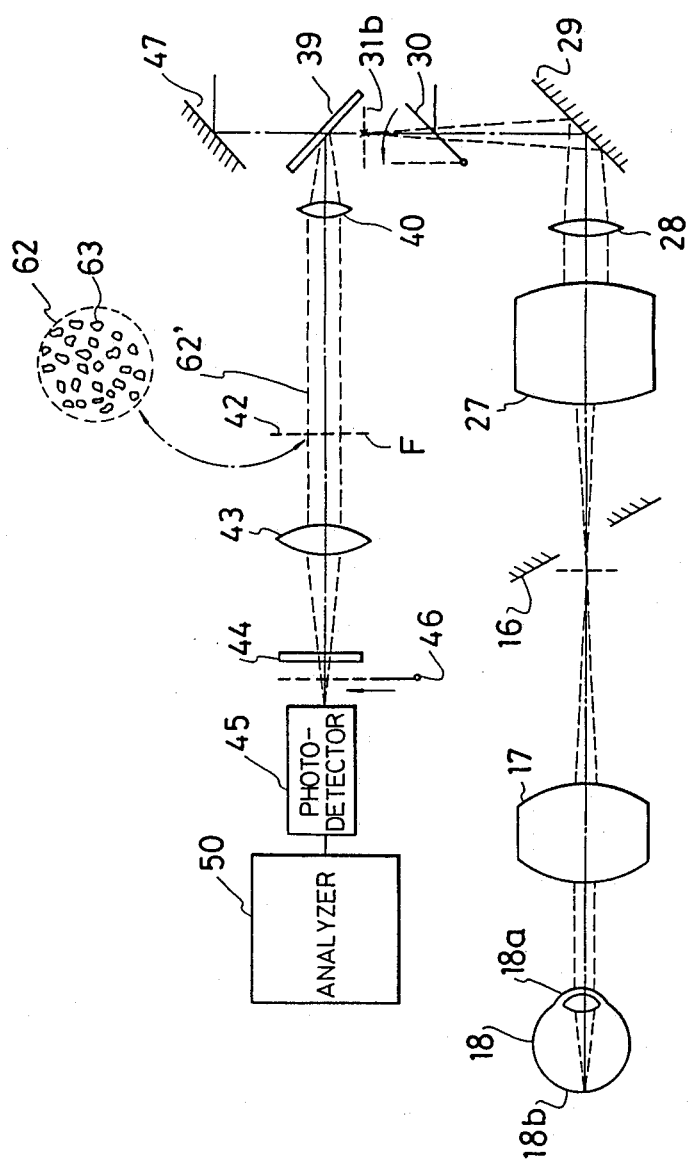
FIG. 6 is an explanatory diagram showing the formation of a diffraction-plane speckle pattern.

This is illustrated by FIG. 6. Only speckle light reflected by the wavelength separation mirror 39 reaches the Fourier-transform plane F, so the diffraction-plane speckle pattern 62 that is obtained is only of the measurement region 61″ illuminated by the laser beam, i.e., there is no light scattered from the surrounding tissue or other blood vessels. It is known that rays of laser light scattered by blood cells moving in the blood vessels in the measurement region 61″ in FIG. 5 arrive in random phase at the Fourier-transform plane F that forms the observation plane, and are superimposed on each other in an interfering manner to form a laser speckle pattern which appears in the form of spatially randomly arranged speckles. It is also known that when the scattering bodies, i.e., the blood cells, are moving at a given velocity, the movement of the speckles thus formed will be proportional to the velocity of the said bodies.

Therefore, also in this case the diffraction-plane speckle pattern 62 will be observed as a pattern in which each of the speckles 63 is distributed at random. Each of the speckles 63 moves according to the blood flow velocity, so that a photodetector 67 detects the speckle movement through a multiple detection aperture pattern 65 constituted of a plurality of small apertures 65′, as shown in FIG. 7b, and through a condenser lens 66. This produces a photon correlation curve corresponding to a time-course fluctuation in speckle light intensity, as shown in FIG. 8b. As a correlation time $\tau c$ (a delay time at which a correlation value attenuates to 1/e) corresponding to the degree of time-course fluctuation will correspond to the velocity of the blood flow, the velocity of the blood flow can be measured by examining this correlation time. With regard to FIG. 7, the diffraction-plane speckles 63 and multiple detection aperture pattern 65 are both on the Fourier-transform plane F.

In a previous application (Japanese Patent Laid-Open Publication No. 63(1988)-242220), because the laser beam 60′ used to illuminate a region 61′ was larger than the diameter of the blood vessel, as shown in FIG. 5, speckle light reflected from surrounding tissue 69 as well as from the blood vessel 68, as shown in FIG. 9, arrive at the detection plane in a superimposed manner to form the speckle pattern. Thus, the speckle signal photoelectrically obtained by the small detection apertures contains noise components which originate from the surrounding tissue and are superimposed on blood flow information from the blood vessel. In addition, these noise components have many light quantities and a great amplitude with the result of a poor measurement.

In the other example as disclosed in Japanese Patent Laid-open Publication No. 63(1988)-242220, the laser speckles reflected not only from the blood vessel 68, but also from the surrounding tissue 69 are received for detection. In this example, the detection is performed through an image-plane speckle pattern which is formed on a conjugate and magnified image plane. The detection on the image plane enables an image of the blood vessel portion 68 to be detected separately from an image of the surrounding tissue 69, thus causing no problem such as in the detection at the Fourier-transform plane. In order to extract blood flow information, it was, however, necessary to align a small detection aperture, such as a pinhole, with the image of the blood vessel to be measured on the magnified image plane, which is a time-consuming procedure. More specifically, in order to align the detection aperture correctly on the magnified image of the blood vessel to be measured while observing the fundus, it was necessary to provide an indicating mark linking the observation eyepiece with the detection aperture and perform the positioning on the target blood vessel within the field of view thereof.

This interlocking mechanism was complex and raised the cost of the apparatus, and had the added drawback that the mechanical adjustment of the indicating mark and the detection aperture during construction was difficult. Also, mechanical play in the linkage produced errors in the positional setting and degraded the operating response. Furthermore, defining the target blood vessel involved a two-stage procedure: first, fixing the vision so that the laser beam illuminates a region that includes the blood vessel, and then using an eye fixation mark to select one blood vessel. However, if in the meantime there was a shift in the detection position caused by movement of the subject's eye, the whole procedure had to be repeated, which was inefficient.

Because a region on the fundus that was larger than the blood vessel was illuminated by the laser beam, so that as shown in FIG. 9 the beam overflowed onto the surrounding tissue, the amount of light scattered by the surrounding tissue was larger than the amount of light scattered by the blood in the blood vessel, making it impossible to accurately differentiate the blood vessel from the surrounding tissue at the magnified image plane. Using spatial frequency filtering in an effort to improve the situation again increases the complexity of the optical system markedly reduces the amount of detected light.

In this embodiment, as shown in FIG. 5, the illuminating laser beam 60 is focused down to a diameter that is around the same as that of the blood vessel, or smaller, and the speckle light at the Fourier-transform plane does not include any scattered light from surrounding tissue, so the speckles 63 reflect only the velocity of the blood flow in the blood vessel.

Therefore, signals containing blood flow information can be detected from the diffraction-plane speckle pattern 62 formed at the Fourier-transform plane F no matter where the detection aperture is positioned, as long as it is within the area of the speckle pattern at the Fourier-transform plane. Selecting the required blood vessel position from among the various blood vessels in the field of view on the fundus only requires that the laser beam be directed at the position concerned, and can be achieved by manipulating the swingable mirror 9 by means of the manipulator 20 shown in FIG. 1. It is also necessary to make the beam the same size or smaller than the diameter of the target blood vessel at the measurement position. Also, as there are individual variations in the size and position of blood vessels, a means of adjusting the size of the beam is required for correct measurement. However, the mechanism becomes complex if it is made to allow a larger range of beam adjustment than necessary, and owing to such factors as aberration of the lenses, the beam becomes ellipsoidal and the intensity distribution of the beam becomes uneven.

Therefore, in this embodiment the size of the beam can be adjusted over a predetermined range. This adjustment can be carried out continuously or in steps by moving the laser focusing lens 7 along the optical axis and using a turret type arrangement for the aperture 6 by means of which the size of the aperture can be changed.

The maximum diameter of a retina blood vessel is usually about 150 micrometers, so preferably the beam can be adjusted to a maximum diameter of 200 micrometers. If it is larger than necessary, unrequired speckle light from adjacent blood vessels or the surrounding tissue will be picked up.

The problem here is that when the beam is moved to the desired position on the fundus, the corresponding position of the speckle pattern light 62' on the Fourier-transform plane also moves. To move the detection aperture accordingly requires the same kind of involved mechanism used in the conventional apparatus. In the present invention, as shown in FIG. 10, an arrangement is used whereby the beam can be moved anywhere within the confines of a specific angle of view range 71 (in FIG. 11, the angle of view 72) that is within the observation and photographic field 70 of the fundus camera and which is also smaller than the angle of view of the observation and photographic field 70 (in FIG. 11, the angle of view 73). As one example, laser beam movement is relatively easy when the measurement is within a range of about 3 mm in diameter in the vicinity of the center of the field of view. Therefore, for measuring at a position outside the range of movement 71, an eye fixation guide or the like may be used to locate the target position in the range 71, which is a simple, straightforward operation.

Next, as shown in FIGS. 12a and 12b, there can be set the angle of view 72 of the diffraction-plane speckle pattern light 62' on the Fourier-transform plane F corresponding to the range 71 within the field of view of the fundus plane S. In this connection, a multiple detection aperture pattern 65 is provided that can easily encompass at least the said range 72 and which has apertures 65' arrayed over an area that is larger than the range 72. With this arrangement, with reference to FIG. 12, when an illuminating laser beam 60a is moved to 60b and 60c, to shift from the illumination position 61a to illumination positions 61b and 61c, corresponding speckle patterns 62a, 62b, 62c of the measurement positions are formed at the Fourier-transform plane F. However, because no matter what the position of the diffraction-plane speckle pattern, it will always be somewhere inside the multiple detection aperture pattern 65 disposed at the same Fourier-transform plane, it is possible to detect which of the apertures 65' at that are giving rise to intensity fluctuation caused by speckle motion, eliminating any need for alignment on the detection plane, i.e., the Fourier-transform plane F. That is to say, with the method of the present invention the laser beam only has to move to the required position within the range that has been set beforehand, while observing the fundus, and that position becomes the measurement position setting, so the operation is direct and highly practical.

Another major feature is that apertures 65' involved in the detection of the motion of speckles 63 in diffraction-plane speckle patterns (such as 62a, for example) formed on the Fourier-transform plane F, has a plurality of detection apertures instead of the single aperture of the prior art.

Therefore, this means that compared with the photon correlation data (FIG. 8a) detected at one point in the diffraction-plane speckle pattern 62 (FIG. 7a) by a single aperture 64, the photon correlation data (FIG. 8b) detected with the same measurement time by the multiple detection aperture pattern 65 constituted of apertures 65' (provided that the diameter of the apertures equals that of the single aperture 64 shown in FIG. 7a) will have a much greater intensity, i.e., it has the advantage of providing an increased amount of light for detection.

When lasers are used as ophthalmic diagnostic devices, safety considerations require that the intensity of the illuminating laser beam be reduced by however small a margin, and that operation using the laser beam is kept as short as possible. Also, to eliminate the effects of eye movement during measurement or of vibration of the overall measurement system and also to reduce the burden on the person undergoing the eye examination, it is essential that the measurement be completed in a short time. However, the light receiving optical system in the eye fundus camera has a large F-number and reflectance of a laser beam on an eye fundus is generally low and is not something that can be artificially controlled, and as such the best method is to improve the light detection sensitivity. In this regard, the present invention has a high degree of utility, as it employs a multiple detection aperture pattern comprised of numerous small apertures used for photon correlation detection.

To summarize the features described above, the laser beam illuminates just the blood flow portion of a blood vessel to produce a speckle pattern formed only of light scattered by blood flow signal components, and this pattern is detected for photon correlation on the basis of numerous points by means of a multiple detection aperture, the surface of which is covered with small apertures. In addition, the detection aperture provided at the detection plane covers a wide range and wherever the position at which the speckle light arrive is moved by moving the beam, the light can always be detected at that position. This makes it easy to select the blood vessel to be measured and to perform the alignment, in addition to which, with the large increase in the amount of detected light it becomes possible to use the speckle method to measure the velocity of the blood flow in a single blood vessel.

The method used to control the laser beam to illuminate a target blood vessel in the eye fundus may appear to be the same as the one used in the laser Doppler method, but in terms of operation and principle there are considerable differences. In one Doppler method the laser beam is split into two beams which are made to intersect at a known angle at the position of the eye fundus blood vessel concerned, while another method using a single beam requires that the angle of beam incidence on the blood vessel or the angle of scattered light detection has to be known beforehand. With the speckle method according to the present invention, no such difficult and time-consuming procedures are required because projection and receiving optical paths of the observation and photography light in the fundus camera can be utilized without modification.

With the laser Doppler method the laser beam is split into two beams which are directed so they intersect at the blood vessel concerned and a Doppler shift frequency corresponding to the velocity of blood cells moving through the interference fringes thus formed is measured, or in the case of a single beam, interference is produced between Doppler shift light scattered by the blood cells and light from a static scatterer provided separately that has no Doppler shift, thereby providing a heterodyne detector for measuring the Doppler shift frequency and determining the velocity of the blood flow. In contrast, the laser speckle method utilizes time-course changes in the intensity distribution of a speckle pattern produced by the superposition of light of random phases scattering from large numbers of cells, which corresponds to blood flow velocity, the degree of said change being measured as a frequency component signal to determine the velocity of the blood flow.

Figure 13:
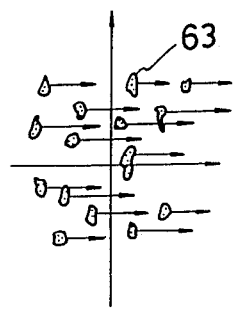
FIGS. 13 and 14 are for illustrating translational and boiling motion speckles, respectively.
Figure 14:
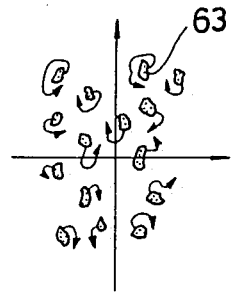

In one example of the prior art in which the motion of a speckle pattern accompanying the movement of a body is detected using a multiple detection aperture constituted of a plurality of small apertures, the object is speckles in translational motion, and interference arising between signals detected from the multiple apertures produces a cross-correlation component. That is, there are two types of speckle pattern motion, translational and boiling. Translational motion, illustrated in FIG. 13, refers to the translation of image plane speckles 63 in a fixed direction without any change of shape. Boiling, illustrated in FIG. 14, refers to a random, flickering motion of the image plane speckles 63, which change shape, disappear and emerge as if bubbling up to the surface.

Figure 15A:
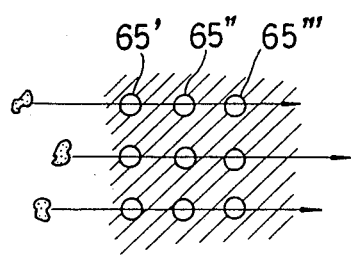
FIGS. 15a and 15b are drawings illustrating translational and boiling motion speckles which cross detection apertures.
Figure 16A:
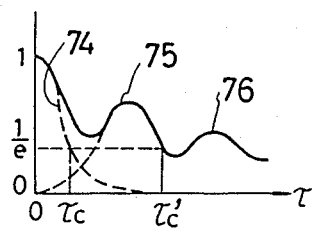
FIGS. 16a and 16b are characteristic curves showing correlation functions of intensity fluctuations produced by speckles crossing the detection apertures.

Employing multiple apertures for speckles in translation, as shown in FIG. 15a, increases the probability that a speckle 63 will cross two adjacent apertures, such as 65' and 65'', or 65'' and 65''', producing a cross-correlation component between the said two apertures. With respect to the photon correlation function as shown in FIG. 16a, as well as the autocorrelation component 74, indicated by the dashed line, of each individual aperture, there is a superposing of the cross-correlation component 75 between adjacent apertures, and of the cross-correlation component 76 between two apertures separated by another aperture. For example, if the spread of the correlation function at a delay time at which the correlation value attenuates to 1/e is expressed as the correlation time, what is $\tau c$ with a single aperture becomes $\tau c'$ with multiple apertures, which is undesirable. To reduce the cross-correlation component, it is necessary to provide sufficient spacing between the multiple apertures to form a state of non-correlation between apertures. The drawback is that it then becomes impossible to dispose a sufficient number of apertures within the range of the speckle pattern light beam, meaning it becomes no different from the conventional detection arrangement employing a single aperture.

Figure 15B:
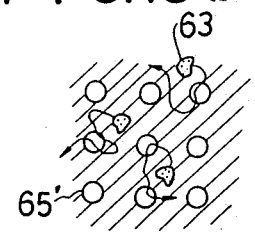
Figure 16B:
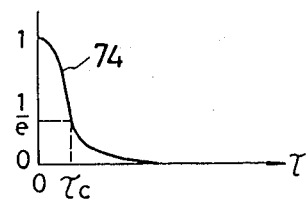

However, from numerous experiments the present inventors noticed that the laser speckle pattern produced by light scattered by the flow of blood in the blood vessels of the eye fundus had a boiling motion. When multiple apertures are employed for speckles with a boiling motion, as shown in FIG. 15b, there is a very low probability that a given speckle 63 will cross two adjacent apertures without changing shape, the result of which is that, as shown in FIG. 16b, the photon correlation function will be only the autocorrelation component 74 of each separate aperture. This autocorrelation component 74 is the same as that obtained in the case of detection using a single aperture, and enables the correct correlation delay time $\tau c$ to be obtained. From the foregoing, applying a multiple detection aperture pattern having numerous small apertures to speckles exhibiting a boiling motion provides the major advantage of enabling an increase in the amount of light used for detecting the same signal component as in the case of a single detection aperture. In this case, the autocorrelation 74 is not dependent on the number of apertures involved in the detection, which gives rise to desirable characteristics owing to the fact that there is no error caused by variance in the number of apertures. Furthermore, the fact that the speckles produced by the blood flow in the eye fundus have a boiling motion is an indispensable part of the present invention.

Because there is no cross-correlation effect the apertures 65' can be positioned relatively close together, with the result that, as shown in FIG. 17a, numerous apertures 65' can be included in the range of the speckle pattern light beam 62 to be detected, which is highly practical. Positioning the apertures 65' too close together, however, can result in one speckle spanning two adjacent apertures 65', as shown in FIG. 17c, giving rise to cross-correlation components. Therefore, as shown in FIG. 17d, the apertures 65' should be separated by a distance that is larger than the average size of the speckles at the detection plane. As speckle size depends on optical system conditions such as magnification factor, F-number or spot size on the eye fundus, the average speckle size at the multiple detection aperture pattern should always be the standard used.

Spacing the apertures too far apart may result in there being only one aperture 65' within the speckle light beam 62 as shown in FIG. 17b, which would be the same as the conventional single aperture system. To avoid this, it is necessary to consider the spread range of the speckle pattern 62 and separate the apertures by a distance that ensures that the detection will be based on the presence of at least two of the apertures 65' within the said range.

Because the diameter of the apertures 65' is set so that it provides the same signal component as when a single detection aperture is used, it is preferable to employ the type of point detection used in the conventional speckle detection method. However, because in practice it is necessary to obtain an amount of light that is to some extent limited, it is known, both theoretically and experimentally, that an aperture may be used that has a smaller diameter than that of the average speckle concerned. In the present invention, also, it is necessary that all the apertures 65' have the same diameter and that the said diameter be smaller than the average speckle size at the detection plane, as shown in FIGS. 17a and 17d. An aperture diameter that is larger than the average speckle size would allow the presence of more than one of the speckles 63 in an aperture 65', as shown in FIG. 17e. In practice this would be undesirable, because the spatial intensity distribution would be affected by the averaging by an amount corresponding to the aperture surface, and although there would be an increase in the direct current portion, the signal portion would be decreased, producing a deterioration of the S/N ratio. This disadvantageously results in deviation of photon correlation data. Considering the above-mentioned facts, it may be preferable to make the speckle size on the speckle pattern relatively large.

The use of the multiple detection aperture according to the invention can also be applied to image plane speckles formed at an image plane that is conjugate with the eye fundus. In the image plane speckles, however, the spot size of the laser beam is very small, more particularly so small as 150 to 200 micrometers in diameter, and is substantially equal to or smaller than the diameter of the blood vessel. This means that a spot image formed by the speckle light at the image plane is the same size if it is imaged in equal size, thus making the averaged size of each of the individual speckles much smaller. Accordingly, this necessitates a multiple detection aperture pattern comprised of a plurality of very small apertures (several micrometers in diameter). This is however impractical in view of the fact that such an aperture pattern is difficult to manufacture, expensive and sophisticated in handling and management against dusts or the like. To compensate for this, a method may be proposed in which a microscopic objective is used for magnification to provide detection at a conjugate and magnified image plane.

This method is, however, not suitable because the incorporation of a magnification imaging system using the microscopic objective into the speckle detecting optical system inevitably makes the optical path longer by an amount of 100 to 150 mm and the whole apparatus complicated by a factor that the optical path must be set considering an optical path due to the beam reflection by mirrors. This method also has the drawback that a slight deviation of the objective causes a great displacement of the magnified image. As shown in FIG. 6, the speckle light from the illuminated spot of the eye fundus is converged at a conjugate image plane (for example at a plane 31b) to produce image plane speckles each size of which is very small. Referring to the Fourier-transform plane, however, the light from the illuminated spot in the eye fundus travels as a diffraction-plane speckle light beam 62' in the expanded parallel form and forms diffraction-plane speckles, each size of which is much greater than in the case of the image speckles. This makes the manufacturing of the multiple detection aperture pattern easy and inexpensive, and advantageously requires no magnification imaging system using the microscopic objective.

If the multiple detection apertures are in a random pattern, the correlation time derived from the photon correlation data depend to a large extent on the randomness of the fabricated pattern and the number of apertures. This will make it difficult to obtain the same signal component no matter where the speckle light falls on the multiple detection aperture pattern, which has an adverse effect on reproducibility and stability and is also undesirable in terms of production efficiency. Also, the unevenness in the intensity distribution of the speckle light beam at the detection plane accompanying the use of a random arrangement cannot be ignored.

Figure 19:
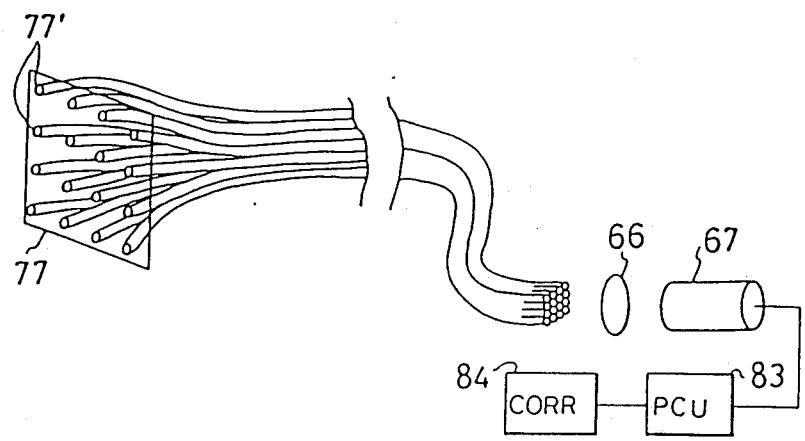
FIG. 19 is a perspective view of another detection aperture arrangement.

In this regard a characterizing feature of the present invention is the regular arrangement of the plurality of small apertures. A lattice arrangement may be used where in which the centers of four adjacent apertures 65' form the four vertices of a rectangle, as shown in FIG. 18a; or as shown in FIG. 18b, a triangular arrangement may be used with the center of each of three adjacent apertures 65' forming the apex points of the triangle. Instead of such apertures, an optical fiber bundle 77' may be used in which each optical fiber has a core diameter equal to the diameter of an aperture, arranged in a multiple detection aperture pattern at an incident plane 77, as shown in FIG. 19. Such an arrangement would allow parts such as the photodetector 67 to be remotely located.

This embodiment uses the arrangement shown in FIG. 7b in which fluctuation in the intensity of the total detected speckle light coming from the apertures 65' is detected for photon correlation as a total fluctuation by a single photodetector 67, via a condenser lens 66. As such, the photoelectrical pulse signal thus obtained from the photon counting unit (PCU) 83 differs instant to instant from photoelectrical pulse signals from individual apertures. However, statistical processing can be used to obtain the same information with respect to the photon correlation, and the multiple detection aperture pattern also has the various advantages mentioned above, such as an increased amount of light.

Figure 20:
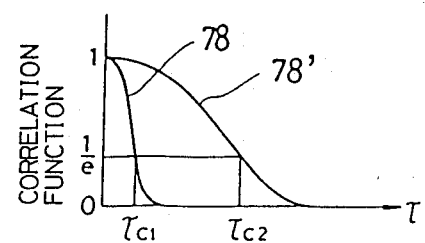
FIG. 20 is a characteristic curve showing a correlation function of a speckle signal.
Figure 21:
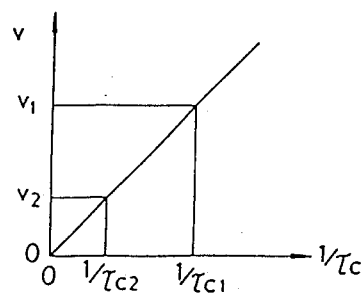
FIG. 21 is a graph used for obtaining a velocity value from the characteristic curve of FIG. 20.

Therefore, in this embodiment the statistical processing of the photoelectrical pulse signals (photon correlation method) is particularly important. However, the usual correlation processing or frequency analysis can be employed, which in practice is highly advantageous. On the other hand, the accuracy of the photon correlation processing depends greatly upon an integrated amount of light determined by the detected amount of light and detection time. In this respect, the present invention is very useful because the detected light quantity increases, thus making the detection time (measuring time) shorter. The photon correlation function, as indicated by a curve 78, exhibits a rapid attenuation in the case of rapid blood flow as shown in FIG. 20 because of rapid boiling motion of the speckles and rapid time-course fluctuation in light intensity, while exhibiting a relatively weak attenuation as indicated by a curve 78' in the case of slow blood flow because of a slow time-course fluctuation in the light intensity. As the reciprocal of the correlation time $\tau c$ is proportional to the velocity, it becomes possible to evaluate the corresponding velocities as shown in FIG. 21. Here, the setting of the factor of proportionality is strongly dependent on the scattering bodies; a reliable value can be set by a prior correction based on another blood flow measurement method such as fluorescent fundus photography, or by using a correction based on a flow of blood through a glass tube that is equivalent to the blood vessel. Even if the factor of proportionality includes some deviation from the true value, the present method provides superior data reproducibility and stability, and as such is highly useful in clinical applications.

In this embodiment it is necessary to adjust the quantity of laser light used to illuminate the eye fundus. However, it is difficult to manually effect a smooth change the light quantity from the pre-measurement alignment level to the level used for measurement. Also, a number of light quantity switching level options is required in view of the individual variations that exist in eye fundus reflectance, crystalline lens turbidity, and so forth, all of which have a bearing on the amount of light to be used for measurement. However, it is difficult to achieve the high-speed sensitivity by means of a single, simple mechanism at the start and finish of the measurements. This problem has been solved in this embodiment by using two separate light quantity adjustment filters 2 and 3.

Figure 22:
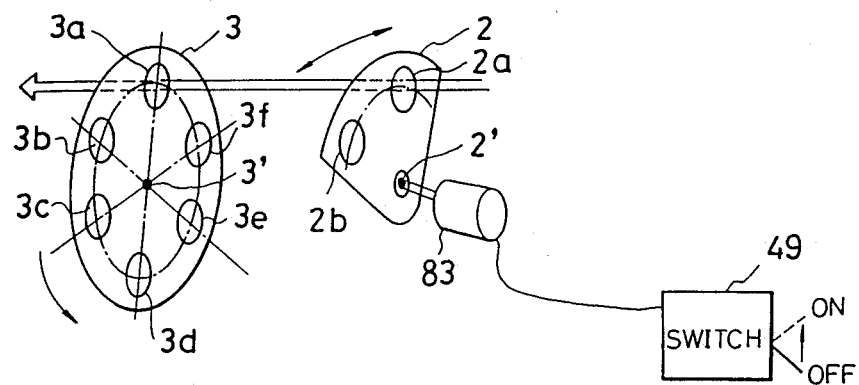
FIG. 22 is a perspective view of a mechanism for adjusting the quantity of light.

With reference to FIGS. 1 and 22, the laser beam from the laser beam source 1 passes through the first light quantity adjustment filter 2 which can be rotated about the axis 2' by fixed angular increments, by means of a solenoid 83 interlocked with the measurement switch 49, for example. When the measurement switch 49 is OFF, filter segment 2a is selected which reduces the light quantity to a level that is low but enough to be perceived by the measurer. When the measurement switch 49 is ON, filter segment 2b is selected, setting the light quantity at a level that is slightly higher than is required for the measurement. Upon completion of the measurement, filter segment 2a is rotated back into the optical axis. Thus, the light quantity can be set promptly at the beginning and end of the measurement procedure.

Light from the filter 2 then passes through the light quantity adjustment filter 3. As one example, the filter 3 can be rotated about the axis 3' in six steps to switch in filter segments 3a to 3f. This is done manually, and in conjunction with the filter segment 2a of filter 2 enables the light quantity required for measurement to be closely adjusted for the measurement object.

Figure 23A:
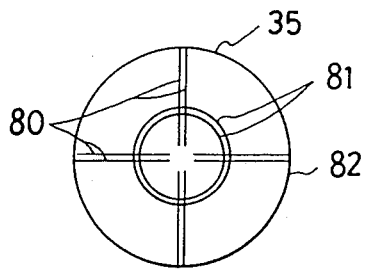
FIGS. 23a to 23c are perspective views of the field of view image of a reticle.

As has been mentioned, the range of movement of the laser beam is limited to within the range 71 of the field of view. It is helpful if the measurer is able to know the said range 71 of laser beam movement on the eye fundus. In this embodiment this information is provided by using the reticle 35 (shown in FIG. 1) adapted by the addition of a double circle 81 to the existing crosshairs, the double circle 81 being used to indicate the said range of laser beam movement, as shown in FIG. 23a. This has the added convenience that the double circle can be used to correct the diopter.

Preferably, the view of the eye fundus should be magnified to facilitate the precise positioning of the laser beam on the blood vessel concerned. Observation will also be aided by using a wider angle of view that provides an overview of the blood vessels of the eye fundus. To achieve this, it is necessary to be able to change the angle of view to match the measurement objective. The light receiving system of an ordinary eye fundus camera is provided with lenses for varying the angle of view. However, this is not suitable for the present apparatus which detects the speckle pattern via the light receiving system, meaning that changing the angle of view would alter the detection conditions by changing the magnification of the image.

Figure 23B:
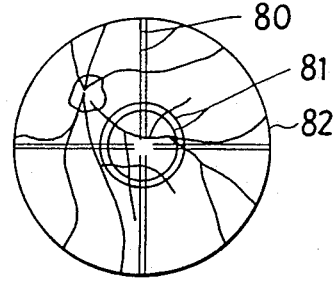
Figure 23C:
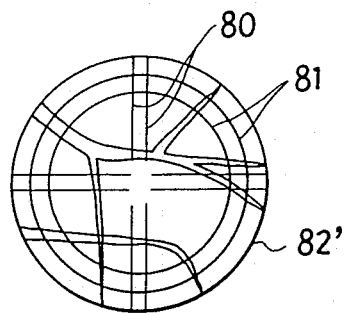

The above objective is attained by providing the observation eyepiece 36 (shown in FIG. 1) with a zoom capability, which enables the magnification of the observation field of view to be smoothly varied without altering the speckle detection system conditions. The minimum magnification can be set to the standard eye fundus camera observation viewing angle, as shown in FIG. 23b, and the maximum magnification should be set in accordance with an angle of view whereby, as shown in FIG. 23c, even at the highest magnification the double circle 81 of the reticle that indicates the range of laser beam movement is within the field of view 82'. Thus, the adjustment of the laser beam position can be observed regardless of whether the zoom-type eyepiece is at a magnified or standard setting.

In previous cases when a eye fundus camera has been utilized for detecting laser speckle light from the fundus, the usual method employed has been to insert a wavelength separation mirror into the optical path of the fundus observation and photography light receiving system during measurement, the said mirror reflecting only light having the same wavelength components as the speckle light.

However, in the case of the present embodiment which is characterized by the use of a multiple detection aperture pattern to provide effective detection over the whole range of the laser beam, the specification of the optical axis of the speckle light detection section is particularly precise, and in measurement operations, too, a high degree of stability is required of the wavelength separation mirror. As such, a method whereby the wavelength separation mirror has to be mechanically operated each time does not meet these requirements.

Specifically, the vibration produced by the retraction of a wavelength separation mirror causes vibration of the optical path along which the speckle light is propagated and is thereby manifested at the detection plane as speckle pattern vibration, and thus ends up as speckle signal noise. As a magnified image system is employed in the detection of the speckle light, the effect of such vibration is particularly pronounced. In addition, the retraction position of the mirror lacks sufficient reproducibility. Also, when the wavelength separation mirror that defines the optical axis of the speckle light detection system is movable, it cannot be adequately aligned and adjusted when the apparatus is being manufactured, and there is also variance from unit to unit. In addition, there is also the concern that frequent use will affect the mechanical instability as a result of age softening and deterioration in service durability.

As has already been explained with reference to FIG. 1, in view of the fact that the detection of speckle light is regarded as a principle function of the present apparatus, the wavelength separation mirror 39 is fixed in position and there are no moveable mirrors that can be moved into the optical path along which the speckle light travels. For observation and photography, a swingable mirror 30 is provided before the wavelength separation mirror 39. Retracting this mirror from the optical path enable the speckle light to be directed into the optical detection system via the wavelength separation mirror 39 which has been fixed beforehand at a precisely predetermined position. Because the mirror 39 is fixed, the optical axis of the speckle light remains stable, enhancing the quality of the measurements.

Manual operation of the observation/photography swingable mirror 30 at the beginning and end of the measurement cannot be effected with sufficient speed and smoothness, and is also subject to human error. Measurement only takes a short time, and it is undesirable if time is wasted operating the mirror 30, as this also increases the chance of the measurement position being shifted by movement of the subject's eye.

This problem is solved in this embodiment by interlocking the swingable mirror 30 with the measurement switch 49 so that when the switch 49 is switched ON the mirror 30 is retracted from the optical path, and when the switch 49 is switched OFF the mirror 30 is inserted into the optical path. Another swingable mirror 34 is also interlocked with the measurement switch so that when the switch is switched ON for measurement, the mirror 34 is similarly retracted from the optical path, allowing light of a wavelength component that is transmitted through the wavelength separation mirror 39 to be used for observation purposes. When measurement is not being performed, switch 49 is OFF and the mirror 34 is located in the optical path and therefore reflects light coming from the lens 33 to enable the light to be observed. It is therefore possible to observe the eye fundus during the measurement process.

Measurement is usually started and ended as a volitional act of the measurer, the precise timing cannot be communicated either to the person undergoing examination or to others involved in the procedure, such as persons handling the signal analysis or assisting in the measurement. This is especially the case when the measurement only takes a second or less, and can therefore be finished before anyone else notices. During the measurement the subject has to cooperate by not moving; there may be cases where signal analyst cannot decide whether an input is a true measurement signal or just noise; and there may be insufficient communication with the others assisting with the measurement.

In the present embodiment an electronically generated sound is used to signal that measurement is in progress. The signal is sound when the measurement switch is switched ON to begin the measurement and when the switch has been turned off and is then turned on to resume measurement, as well as when the measurement is carried out from start to finish without a break. Thus, the signal enables the precise time at which the measurement is started and stopped to be communicated to all participants, thereby solving the above problems and enhancing the utility of the apparatus.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention should not be limited to the particular embodiment disclosed as the best mode contemplated for carrying out the invention, but that the invention will include all embodiments falling within the scope of the appended claims.

What is claimed is:

1. An ophthalmological diagnosis method in which the eye fundus is illuminated with a laser beam of a predetermined diameter, and light scattered and reflected from the eye fundus is evaluated to measure the blood state in the eye fundus tissue, comprising the steps of:

illuminating a blood vessel to be measured with the laser beam of a predetermined beam spot whose diameter is substantially equal to or smaller than that of the blood vessel;

converging light scattered and reflected by blood cells flowing through the blood vessel illuminated by the laser beam to form diffraction-plane speckles at a Fourier-transform plane relative to the eye fundus which is taken as an object plane;

detecting boiling motion of the diffraction-plane speckles through a detection aperture disposed at the Fourier-transform plane and formed thereon with a multiple detection aperture pattern comprised of a plurality of small apertures; and evaluating a speckle signal produced by a photodetector depending upon a fluctuation in a total amount of light passing through each of the small apertures on the multiple detection aperture pattern to measure velocity of the blood flowing through the blood vessel concerned.

2. A method as set forth in claim 1, wherein the fluctuation in the total amount of light passing through each of the small apertures on the multiple detection aperture pattern is detected by means of a photon correlation method to derive therefrom a photon correlation function having a correlation time whose reciprocal is multiplied by a predetermined factor to measure velocity of the blood flowing through the specific blood vessel.

3. A method as set forth in claim 1, wherein the distance between said small apertures and/or the diameter thereof is made dependent on the size of the speckle light pattern.

4. A method as set forth in claim 1, wherein said small apertures are arranged on the detection aperture in a predetermined array.

5. A method as set forth in claim 1, wherein said small apertures are distributed over a range within which the speckle pattern is formed.

6. A method as set forth in claim 1, wherein said multiple detection aperture pattern is formed by a plurality of optical fibers each having its diameter made substantially equal to the diameter of each of said small apertures.

7. An ophthalmological diagnosis apparatus in which the eye fundus is illuminated with a laser beam of a predetermined diameter, and light scattered and reflected from the eye fundus is evaluated to measure the blood state in the eye fundus tissue, comprising:

a laser source for producing a laser beam;

optical means for illuminating a blood vessel to be measured with the laser beam produced by said laser source and having a predetermined beam spot whose diameter is substantially equal to or smaller than that of the blood vessel;

optical means for converging light scattered and reflected by the eye fundus to form diffraction-plane speckles at a Fourier-transform plane relative to the eye fundus which is taken as an object plane;

a detection aperture disposed at the Fourier-transform plane and formed thereon with a multiple detection aperture pattern comprised of a plurality of small apertures;

means for photoelectrically detecting boiling motion of the diffraction-plane speckles through said detection aperture to extract a fluctuation in a total amount of light passing through the multiple detection aperture pattern; and means for evaluating a speckle signal obtained by said detecting means to measure the velocity of the blood flowing through the blood vessel concerned.

8. An apparatus as set forth in claim 7, further comprising means for moving said laser beam across a predetermined area within the eye fundus.

9. An apparatus as set forth in claim 8, wherein said small apertures are arranged within a range which corresponds to said area and within which said diffraction-plane speckles are formed.

10. An apparatus as set forth in claim 9, further comprising means for producing a pattern indicative of said range within which said laser beam is movable, said pattern being displayed on a diopter correcting reticle patter to enable a diopter correction.

11. An apparatus as set forth in claim 7, further comprising switching means for initiating measurement, a first filter for adjusting the intensity of the laser beam spot to an intensity necessary for the measurement and to a low intensity, respectively, when the switching means are turned on and off, and a second filter for adjusting the intensity of the laser beam spot passing through the first filter.

12. An apparatus as set forth in claim 7, including means for observing and photographing light to passing through said wavelength separation means.

13. An ophthalmological diagnosis apparatus in which the eye fundus is illuminated with a laser beam of a predetermined diameter, and light scattered and reflected from the eye fundus is evaluated to measure the blood state in the eye fundus tissue, comprising:

a laser source for producing a laser beam;

optical means for illuminating a blood vessel to be measured with the laser beam produced by said laser source and having a predetermined beam spot whose diameter is substantially equal to or smaller than that of the blood vessel;

optical means for converging light scattered and reflected by the eye fundus to form diffraction-plane speckles at a Fourier transform plane relative to the eye fundus which is taken as an object plane;

a detection aperture disposed at the Fourier-transform plane and formed thereon with a multiple detection aperture pattern comprised of a plurality of small apertures;

means for photoelectrically detecting boiling motion of the diffraction-plane speckles through said detection aperture to extract a fluctuation in a total amount of light passing through the multiple detection aperture pattern; and means for detecting a fluctuation in a total amount of light passing through each of the small apertures on the multiple detection aperture pattern by means of a photon correlation method to derive therefrom a photon correlation function having a correlation time whose reciprocal is multiplied by a predetermined factor to measure the velocity of the blood flowing through the specific blood vessel.

* * * * *